United States Patent [19]

Vogeley

[11] 4,003,642
[45] Jan. 18, 1977

[54] OPTICALLY INTEGRATING OCULOMETER

[75] Inventor: Arthur W. Vogeley, Yorktown, Va.

[73] Assignee: Bio-Systems Research Inc., Yorktown, Va.

[22] Filed: Apr. 22, 1975

[21] Appl. No.: 570,853

[52] U.S. Cl. .................................. 351/6; 250/578
[51] Int. Cl.² ...................................... A61B 3/10
[58] Field of Search ............ 351/6, 7, 39; 250/206, 250/221, 578; 340/279; 350/190, 199, 201

[56] References Cited

UNITED STATES PATENTS

| | | | |
|---|---|---|---|
| 2,948,890 | 8/1960 | Barth et al. | 250/221 X |
| 2,966,823 | 1/1961 | Trimble | 350/199 X |
| 3,462,604 | 8/1969 | Mason | 351/6 X |
| 3,712,716 | 1/1973 | Cornsweet et al. | 351/6 X |
| 3,746,432 | 7/1973 | Mason | 351/6 |
| 3,804,496 | 4/1974 | Crane et al. | 351/6 |
| 3,864,030 | 2/1975 | Cornsweet | 351/7 |

Primary Examiner—Paul A. Sacher
Attorney, Agent, or Firm—Martin Fruitman

[57] ABSTRACT

An improved oculometer yielding simplified data accumulation and reduction techniques because of the use of a cylindrical lens system which optically integrates the light reflected from the eye being studied. The use of the cylindrical lens system and a linear sensing element reduces the location data required by a factor of a square root and makes digital processing of the information practical.

5 Claims, 2 Drawing Figures

OPTICALLY INTEGRATING OCULOMETER

BACKGROUND OF THE INVENTION

Numerous oculometers or eye-trackers exist in the patent literature. While there exist several methods for following the movements of the eye, such as tightly fitting contact lenses and measurement of minute voltages generated in the region of the eye, the most satisfactory methods available have depended upon the use of radiant energy reflected from the eye. Such reflection dependent methods are either visible light, ultraviolet or infrared radiation and function on the basis of the difference in reflectivity of various portions of the eye. U.S. Pat. No. 3,462,604 shows an example of such an oculometer. The difficulties which are present in the typical reflection oculometer center on the complexity and the lack of sensitivity of the sensing system. An apparatus based on U.S. Pat. No. 3,462,604 typically contains a light source of approximately 100 watts, most of which is lost in heat and other unwanted radiation. Much of the energy is lost in passing through a multiplicity of filters and lenses and other optics before the radiation reaches the eye.

A further difficulty is encountered in the presently used image sensing system. Typically the image of the eye is projected upon the face of a vidicon tube being used in a conventional TV camera. Such a system uses the typical scanning circuitry associated with such a camera and then uses a converter to change the analog information furnished by the camera to digital information which may be used, with complex algorithms, by a computer to produce the analysis of eye-direction information. This method requires the processing of a vast amount of data and also requires a time lag during the scanning operation which may cause the loss of valuable information.

Limitations in sensitivity of such devices as camera tubes also severly limit the eye space which may be monitored. The typical system yields a monitored space of only about one cubic inch. The present method of overcoming the limitation is by the use of servo-controlled mirrors or lenses to follow the eye, as is shown in U.S. Pat. No. 3,462,604 and U.S. Pat. No. 3,804,496. These methods add even greater complexity to the problem of data reduction and furthermore add possibilities of error.

SUMMARY OF THE INVENTION

It is an object of this invention to provide an improved method and apparatus which greatly simplifies the data reduction problem associated with reflection oculometers.

It is another object of this invention to provide a method and apparatus for eye-tracking which is capable of matching the amount of data processed with the data required for the ultimate application in order that there be no surplus data capability in the system.

It is a further object of this invention to provide a method and apparatus which overcomes speed of response problems and which increases the sensitivity of oculometers so that very low power radiation sources may be used.

It is a still further object of this invention to provide a method and apparatus capable of trading off sensitivity for other desireable characteristics such as field of view and low power consumption.

These benefits are accomplished by the use of cylindrical lens systems, linear sensor arrays and catadioptric lens arrangements. In one embodiment of the invention, a low power consumption light emitting diode with a predominantly infra-red spectral generation is used as a source. This radiation is focused and directed toward the eye by a catadioptric reflector system which also captures the radiation returning from the eye and directs it to a beamsplitter. The beams from the beamsplitter are each processed by a cylinder lens system. This cylinder lens system has the property of collapsing one dimension of the viewed field to a narrow image without affecting the traverse axis. The resulting image is similar to that which results from a television receiver with a malfunctioning vertical deflection system where all the vertical and horizontal information is available but the vertical information is collapsed into a very small height.

In the present invention the cylindrical lens systems process the two beams so that one beam has the vertical information compressed and the other beam has the horizontal information compressed. This compression, or optical integration, then permits the use of sensors which are essentially linear, with no second dimension of any consequence. The use of linear sensors reduces the data reduction problem, to a degree such that, using the same resolution, the data handled is reduced to a factor of twice the square root of the previous factor. For instance, in the typical TV scanned oculometer an approximate 500 vertical line TV raster is used, and if a similar resolution is assumed for the horizontal direction, a data field of 250,000 bits is required. The same visual field with the same resolution can be processed with the use of only 1,000 data bits by the use of the present invention. Moreover, the compression of field in each direction yields the further advantage of increased intensity along the linear image as compared to the previous full field image. This effectively increases the radiation intensity viewed by each sensing element.

The preferred embodiment uses a multiplicity of simple photosensitive elements, arranged in a linear array, at the image plane of the cylindrical lens sytem. This apparatus yields a significant portion of its data directly in digital form and thereby permits direct processing of the visual information by computer. However, if only simple control functions are required, a very limited resolution apparatus can be constructed which contains only a few photodetectors in each linear array and can directly drive a specially designed digital control unit.

It is readily apparent that similar trade-offs can be accomplished with power consumption, speed of response and field of view, so that the invention yields a highly versatile and economic improvement on eye-tracking methods and apparatus.

DETAILED DESCRIPTION OF THE INVENTION

Figure 1:
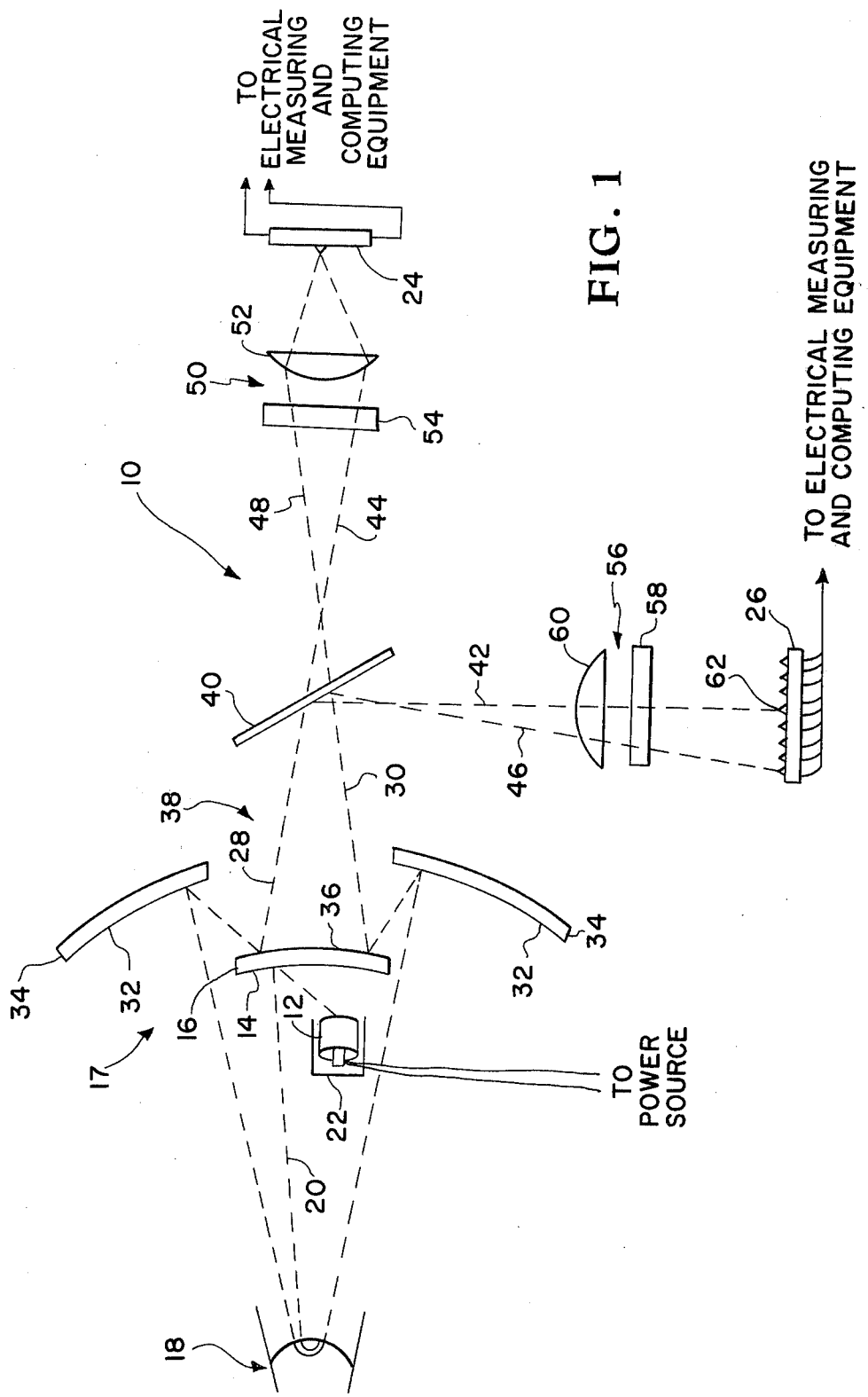
FIG. 1 is a schematic representation of the preferred embodiment of the invention and its mode of operation.

The preferred embodiment of the invention selected for illustration is shown in FIG. 1 in schematic form along with the various optical paths which facilitate the description of its operation. Oculometer 10 uses a light source 12 to generate either visible, infra-red, or other radiation which reflects from near surface 14 of reflection element 16 of catadioptric lens system 17 and is focused and directed to the observers eye 18 as shown by optical path 20. Light from light source 12 is directed toward near surface 14 by cover 22 which also prevents any stray radiation from acting in the system. In the preferred embodiment shown, light source 12 is a Light Emitting Diode which generates infra-red radiation particularly suited for the linear sensors 24 and 26 and which draws minimal power from its power source, not shown. Light source 12 can also be a tungsten lamp or several Light Emitting Diodes. The choice of light source is dependent upon the design requirements or limitations on the oculometer, such as power requirements or sensitivity and upon the spectral sensitivity of linear sensor arrays 24 and 26.

Light reflecting from both the cornea and retina of the observers eye 18 on optical paths 28 and 30 is reflected by near surface 32 of reflector 34 and reflected again by far surface 36 of reflector 16 so that it passes through hole 38 in the center of reflector 34 and strikes beam splitter 40.

Beam splitter 40 divides each light beam striking it into two approximately equal parts. Beam splitter 40 passes half of the intensity of the beam directly through and reflects half the beam so that equal portions 42 and 44 of beam 28 and equal portions 46 and 48 of beam 30 continue beyond beam splitter 40. Beams 44 and 48 enter cylindrical lens system 50 and by the action of cylindrical lens 52 and compensating lens 54, one dimension of the field, as shown by beams 44 and 48, is compressed relative to the transverse field, that which would go into the paper. The effect on the transverse field is best shown at cylindrical lens system 56 where beams 42 and 46 are processed by cylindrical lens 56 and compensating lens 60. In this portion of oculometer 10 the dimensional compression takes place in the plane transverse to the paper and beams 42 and 46 pass through cylindrical lens system 56 essentially without compression. Each of the lens systems 50 and 56 compresses only one dimension of the field relative to the other, but since each cylindrical lens system compresses a different dimension, the original reflection leaving the eye is converted into two essentially linear displays of information. While it is typical that these two displays be of transverse dimensions, this is not a limitation, since in specific applications other relationships between the compressed optical fields may be desired.

With the optical field compressed or optically integrated so that beyond the cylindrical lens systems the displays are simple lines with varying intensities, linear sensor arrays 24 and 26 are all that is required to furnish the total data available to the electrical measuring and computing equipment (not shown). At linear sensor array 26 essentially no dimension exists perpendicular to the paper. Cylindrical lens system 56 has for example, combined all the former picture elements of beam 42 in that dimension perpendicular to the paper into one light spot 62 which is the sum of all the picture elements that formerly existed in the other dimension. Since light spot 62 is the sum of many former elements it is much brighter than any single previous element and that brightness can be used to either reduce the required intensity of the original light source 12 or to reduce the required sensitivity of light sensor arrays 24 and 26 as compared to oculometers where the light sensors view an entire two dimensional optical field.

Figure 2:
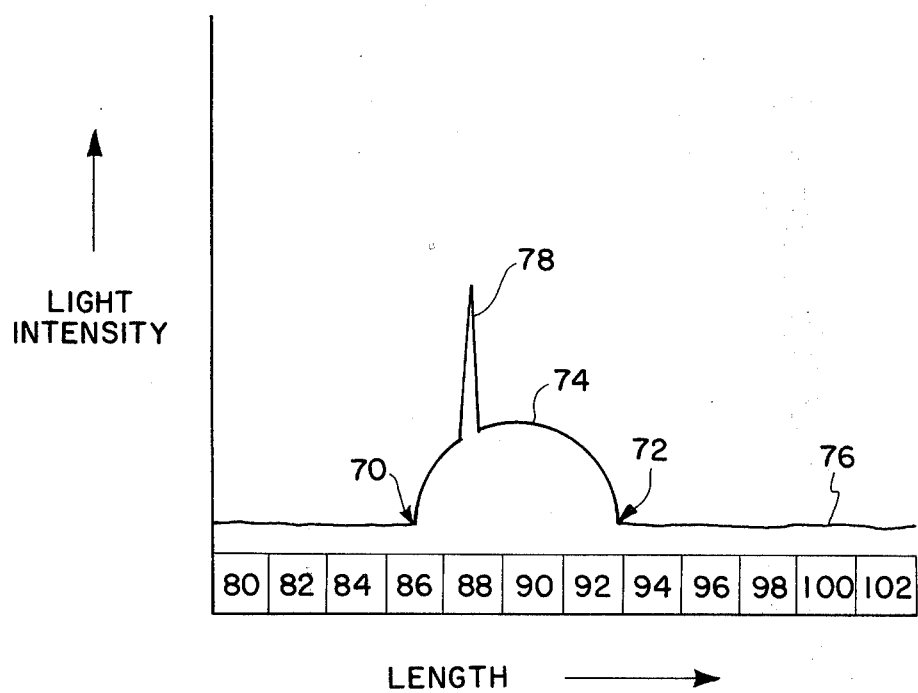
FIG. 2 is a graphical representation of a light intensity profile reflected from the eye.

The optical integration of the optical field is possible in an oculometer because, as shown in FIG. 2, the profile of the information required for processing is relatively simple. FIG. 2 is a plot of the intensity of reflected light across any diameter of the pupil of an observers eye when the eye is subjected to a light source in a manner as shown in FIG. 1. There are two break points 70 and 72 at which the light intensity 74 of the retinal reflection passing back through the pupil deviates from the background light 76. These break points 70 and 72 are all that are required to determine the location and size of the pupil and since the pupil as seen by the oculometer is always roughly elliptical, compressing the entire optical field into one line emphasizes the break points and makes pupil location more apparent. Corneal Reflection point 78 is similarly emphasized by optical integration because it too is always a single area. Thus the process of compression of the optical field not only reduces the amount of data which is required to be processed but also makes that data more distinguishable from background noise.

Linear sensor arrays 24 and 26 consist essentially of many individual small light sensors arranged in linear fashion so that the array is only one sensor wide, but as long as is required for the total number of sensors. In FIG. 2 this array is represented by individual areas 80 through 102. Since the light intensity graph is a reasonable representation of the light falling upon the linear sensor elements 80 through 102, it is clear that the individual electrical output of each light sensor element will locate the corneal reflection 78 and the pupil 74. In the example shown sensors 80 through 84 and 94 through 102 will yield very little electrical output while sensors 86 through 92 will yield a considerable electrical output and thereby indicate the location and size of pupil 74. Sensor 88 will yield the greatest output and therefore indicate the position of corneal reflection 78. Should finer resolution of the positions be required, it is only necessary to reduce the size of the individual sensor elements relative to the pupil size, thereby permitting the number of elements to be increased. Since the system shown in FIG. 1 optically integrates and senses two dimensions of a field view, typically the horizontal and vertical dimensions, the line of sight of the observers eye and the complete location and size of the pupil can be determined by simple digital computer devices.

For some applications fine resolution is not required and in such applications the use of optical integration and linear sensors greatly reduces the amount of data which would otherwise need to be processed. For example, a telephone dialing device for invalids which could use an oculometer would only be required to differentiate between ten locations at which the eye might be looking. An oculometer based on a TV camera would nevertheless be required to process thousands of bits of data information. However, an oculometer based on the present invention would be effective in the same task with the processing of fewer than 100 bits of data. Conventional TV systems are generally constructed with a data potential of approximately 250,000 resolution elements and it is economically unfeasible to build special systems for oculometer use. However, an oculometer using optical integration and linear sensors can be designed for exactly the resolution required for each application with no surplus data capability.

It is to be understood that the form of the invention herein shown is merely a preferred embodiment. Various changes may be made in the shape, size or arrangements of parts; equivalent means may be substituted for those illustrated and described and certain features may be used independently from other features without departing from the spirit and scope of the invention. For example, lens systems other than a catadioptric lens may be used to direct the light to the eye, or a single cylindrical lens system and linear sensor may be used for limited data accumulation. Moreover, light or radiation sources other than Light Emitting Diodes may be used where power requirements are not a limitation.

What is claimed as new and desired to be secured by Letters Patent of the United States is:

1. An improved oculometer which comprises:
   radiation source means;
   directing means for focusing and directing the emissions from said radiation source onto an observers eye;
   optical integration means which processes the reflections from the observers eye by compressing the optical field in at least one dimension so that the optical field of the reflections is converted into a linear form with varying light information along its length; and
   linear sensing array means comprising a series of individual sensing elements upon which the linear form of the reflections are focused which yield electrical information varying with the intensity of radiation falling on the individual elements of the array.

2. An improved oculometer as in claim 1 wherein said optical integration means is at least one cylindrical lens system comprising a cylindrical lens and a compensating lens.

3. An improved oculometer as in claim 1 wherein said radiation source means is at least one light emitting diode.

4. An improved oculometer as in claim 1 wherein said optical integration means includes a beam splitter to form two resulting beams from the reflections from the observers eye; and two cylindrical lens systems, one cylindrical lens system to optically integrate each of said resulting beams, and wherein said linear sensing array means includes two linear sensing arrays one for each of said resulting beams.

5. An improved oculometer as in claim 4 wherein the resulting beams are optically integrated to produce lines which represent perpendicular dimensions of the original optical field.

* * * * *